(12) United States Patent
Barton

(10) Patent No.: US 12,169,326 B2
(45) Date of Patent: *Dec. 17, 2024

(54) SYSTEM AND METHOD OF PROVIDING CUSTOM-FITTED AND STYLED EYEWEAR BASED ON USER-PROVIDED IMAGES AND PREFERENCES

(71) Applicant: ELECTRIC AVENUE SOFTWARE, INC., Solana Beach, CA (US)

(72) Inventor: David Barton, Solana Beach, CA (US)

(73) Assignee: ELECTRIC AVENUE SOFTWARE, INC., Solana Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/725,504

(22) Filed: Apr. 20, 2022

(65) Prior Publication Data

US 2022/0404644 A1    Dec. 22, 2022

Related U.S. Application Data

(63) Continuation of application No. 16/252,313, filed on Jan. 18, 2019, now Pat. No. 11,347,085, which is a continuation of application No. 15/591,754, filed on May 10, 2017, now Pat. No. 10,222,636, which is a continuation of application No. 14/801,024, filed on
(Continued)

(51) Int. Cl.
| | |
|---|---|
| *A61B 3/00* | (2006.01) |
| *A61B 3/10* | (2006.01) |
| *A61B 3/11* | (2006.01) |
| *G02C 3/00* | (2006.01) |
| *G02C 7/00* | (2006.01) |
| *G02C 7/02* | (2006.01) |
| *G02C 13/00* | (2006.01) |

(52) U.S. Cl.
CPC .......... *G02C 13/005* (2013.01); *A61B 3/0025* (2013.01); *A61B 3/0033* (2013.01); *A61B 3/111* (2013.01); *G02C 13/003* (2013.01)

(58) Field of Classification Search
CPC ..... A61B 3/0025; A61B 3/0033; A61B 3/111; G02C 13/005; G02C 13/003
USPC .............. 351/159.73–159.76, 178, 204, 227
See application file for complete search history.

(56) References Cited

U.S. PATENT DOCUMENTS

| | | | | |
|---|---|---|---|---|
| 2014/0270374 A1* | 9/2014 | Unzueta | ............... | G06V 40/171 382/103 |
| 2015/0055086 A1* | 2/2015 | Fonte | ...................... | G06F 16/22 700/98 |
| 2015/0199558 A1* | 7/2015 | Gadot | ...................... | G06T 11/60 382/103 |

\* cited by examiner

*Primary Examiner* — Mahidere S Sahle
(74) *Attorney, Agent, or Firm* — Pillsbury Winthrop Shaw Pittman, LLP

(57) ABSTRACT

The invention relates to systems and methods for providing custom-fitted and styled wearable items such as eyewear based on measurements made from a user-provided image that is resized using a predefined reference that includes an image of an actual wearable item. The eyewear may be provided to a user, who wears the eyewear and provides an image of the user wearing the eyewear. The user-provided images may be compared to a predefined reference (e.g., an image of the eyewear) having a known scale and/or dimension. For example, a user-provided image may be overlaid with the predefined reference and resized so that the wearable item worn by the user in the user-provided image matches (the size of) the wearable item in the predefined reference. Because the scale and/or dimensions of the predefined reference are known, one or more measurements associated with the user may be made based on the user-provided image.

20 Claims, 9 Drawing Sheets

Related U.S. Application Data

Jul. 16, 2015, now Pat. No. 9,671,625, which is a continuation of application No. 14/464,088, filed on Aug. 20, 2014, now Pat. No. 9,086,582.

SYSTEM AND METHOD OF PROVIDING CUSTOM-FITTED AND STYLED EYEWEAR BASED ON USER-PROVIDED IMAGES AND PREFERENCES

CROSS-REFERENCE TO RELATED APPLICATIONS

This application is a continuation of U.S. patent application Ser. No. 16/252,313, filed Jan. 18, 2019. U.S. patent application Ser. No. 16/252,313 is a continuation of U.S. patent application Ser. No. 15/591,754, filed May 10, 2017, which is a continuation of U.S. patent application Ser. No. 14/801,024, filed Jul. 16, 2015, now U.S. Pat. No. 9,671,625, which is a continuation of U.S. patent application Ser. No. 14/464,088, filed Aug. 20, 2014, now U.S. Pat. No. 9,086,582. The entire content of each aforementioned patent filing is hereby incorporated by reference.

FIELD OF THE INVENTION

The invention relates to systems and methods of providing a custom-fitted and styled wearable item such as eyewear based on measurements made from a user-provided image of the user wearing the wearable item that is overlaid onto and resized based on a predefined reference image that includes a full-scale representation of the wearable item.

BACKGROUND OF THE INVENTION

Selecting wearable items can be a highly subjective process to find the right style, color, or other characteristic that suits the taste of a consumer. For example, when shopping for eyewear, users may visit a brick-and-mortar store to try on and make their selections. When shopping for prescription lenses (e.g., vision-corrective lenses) to be fitted onto their selected frames, a user must typically be measured by a professional such as an optician to craft prescription lenses that fit onto the selected frame, as well as take into account the position of the user's pupils with respect to the lenses to ensure proper vision correction.

Such measurements may include, for example, a binocular pupillary distance ("PD"), a monocular pupillary distance, an ocular center ("OC") height, a segment height, and/or other measurements. A PD includes a distance from the center of one pupil to the center of another pupil. A mono PD is the distance from the center of a pupil to the center line of the nose bridge or centerline of the frame bridge. An OC Height includes a distance from the farthest bottom inside edge of the frame to the center of the pupil when eyes are focused straight ahead. A Segment height includes a height of the segment for bifocal, trifocal, progressive, and similar lenses. The Segment height is measured from the line of the segment to the farthest bottom inside edge of the frame.

Although online shopping (e.g., Internet-based electronic retail) has made it more convenient to view various styles and selections of frames, oftentimes it is still difficult for users to visualize how the frames would look while being worn by the user. Furthermore, conventional online shopping for eyeglass frames used for vision correction is further limited by the need for an optician to make measurements of the user wearing the frames to ensure proper lens construction. These and other drawbacks exist with conventional shopping systems and methods for wearable items.

SUMMARY OF THE INVENTION

The invention addressing these and other drawbacks relates to systems and methods of providing a custom-fitted and styled wearable item such as eyewear based on measurements made from a user-provided image of the user wearing the wearable item that is overlaid onto and resized based on a predefined reference image that includes a full-scale representation of the wearable item. The predefined reference image may include a wearable item representation that is used to line up with the user-provided image of the wearable item being worn by the user. The wearable item representation may include a graphical representation (e.g., a wireframe, a Computer Aided Design, a sketch, etc.), an actual image (e.g., a photograph), and/or other representation of the wearable item by itself (e.g., not worn). The predefined reference image may be full-scale such that measurements that are made using the image of the wearable item representation are 1:1 with the actual wearable item.

A given wearable item may have a corresponding predefined reference image associated with it so that measurements using a user-provided image of a user wearing a given wearable item may be obtained by resizing the user-provided image according to a corresponding predefined reference image.

To allow a user to try on a wearable item (e.g., for online implementations), an actual wearable item may be provided (e.g., shipped) to a user, who wears the actual wearable item, obtains one or more images of the user wearing the actual wearable item, and provides the one or more images for processing. A user-provided image may be compared to a predefined reference image that corresponds to the wearable item being worn by the user. For example, a user-provided image may be overlaid with the predefined reference image and resized so that the actual wearable item worn by the user in the user-provided image matches (the size of) the actual wearable item in the predefined reference image. Because the scale and/or dimensions of the predefined reference image are known, one or more measurements associated with the user may be made when the user-provided image is matched with the predefined reference image as if the measurements were made directly on the user wearing the wearable item. The one or more measurements may be made based on an anatomical feature of the user in relation to the wearable item.

The systems and methods may be used in various contexts in which a wearable item is used to make measurements of a user wearing the wearable item. By way of illustration and not limitation, the wearable item may include an eyeglass frame (also referred to as "eyeglass frames") that is used to determine one or more measurements related to the eyeglass frame. In particular, the one or more measurements may be used to custom-fit lenses to the eyeglass frames. More particularly, the measurements may be used to custom-fit prescription lenses to the eyeglass frames. Such measurements may include, for example, a binocular PD, a monocular PD, an OC height, a segment height, and/or other measurements related to an anatomical reference feature such as a pupil and a wearable item such as an eyeglass frame.

The systems and methods allow an entity, such as an eyewear retailer, to provide custom-fitted and/or styled eyewear to the user by determining one or more measurements associated with the user based on user-provided images of the user wearing an eyeglass frame. To custom-style or otherwise select candidate eyeglass frames, the eyewear retailer may obtain user profile information associated with the user. The user profile information may include preference and other information that describes a user. Once obtained, the user profile information may be stored and updated as necessary in a database.

The eyewear retailer (e.g., a stylist working for the eyewear retailer) may determine one or more frame styles and/or colors that, in the stylists' view, would be suitable for the user based on the user preference information. Alternatively or additionally, the user preference information may expressly indicate a preferred frame style (e.g., after perusing an online catalog of frame styles offered by the eyewear retailer). In any event, a set of one or more eyeglass frames may be selected for the user. An identification of each of the selected eyeglass frames may be stored in association with user identifying information so that the system may later retrieve this information (to know which eyeglass frames were selected for the user).

The eyewear retailer may provide the set of eyeglass frames to the user. For example, the eyewear retailer may ship the set of eyeglass frames to the user's home or other address (in brick-and-mortar implementations, the set of eyeglass frames may simply be worn by the user in-store). After having tried on each of the set of eyeglass frames, the user may select a favorite one (or more) to purchase.

To obtain measurements necessary to craft prescription lenses for the selected eyeglass frames, the eyewear retailer may obtain an image of the user wearing the eyeglass frames. The image of the user wearing the eyeglass frames may be associated with user identifying information and frame identification information. In this manner, the eyewear retailer may obtain an identity of both the user and the frame being imaged.

To obtain an image of the user wearing the eyeglass frames, the eyewear retailer may provide or otherwise make available a client application (e.g., a mobile application that executes on the user's mobile device such as a smartphone) that assists the user to take appropriate images of the user wearing an eyeglass frame. The client application may, for example, provide guidance information on a user interface that assists a user to take an appropriate image of an anatomical feature such as a pupil in relation to a wearable item such as an eyeglass frame.

The eyewear retailer may obtain and process the images to determine one or more measurements used to construct lenses (e.g., prescription lenses) to be custom-fitted for the eyeglass frame. For example, a server computing device, with or without assistance from an operator, may resize the image of the user wearing an eyeglass frame based on a predefined reference image that includes an image of the eyeglass frame in full-scale. The full-scale predefined reference image may be used to resize the image of the user wearing the eyeglass frame so that measurements may be made using the resized image. Alternatively or additionally, the predefined reference may include an image of the eyeglass frame not in full-scale, but with a scaling offset (e.g., 110% of full-scale). In these instances, the image of the user wearing an eyeglass frame may be resized using the predefined reference, but the measurements may be transformed using the scaling offset and/or known dimensions of the predefined reference image.

Various parties may benefit from the use of the systems and methods disclosed herein. For example, a user may obtain prescription lenses custom-fitted to custom-styled (e.g., custom-selected) frames without the need to visit a professional such as an optician. An entity such as an electronic (e.g., Internet-based) retailer and others may use the system to provide a convenient and accurate way to provide custom-fitted and/or custom-styled eyewear through the Internet or other electronic (or brick-and-mortar) retail channel.

These and other objects, features, and characteristics of the system and/or method disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE INVENTION

Figure 1:
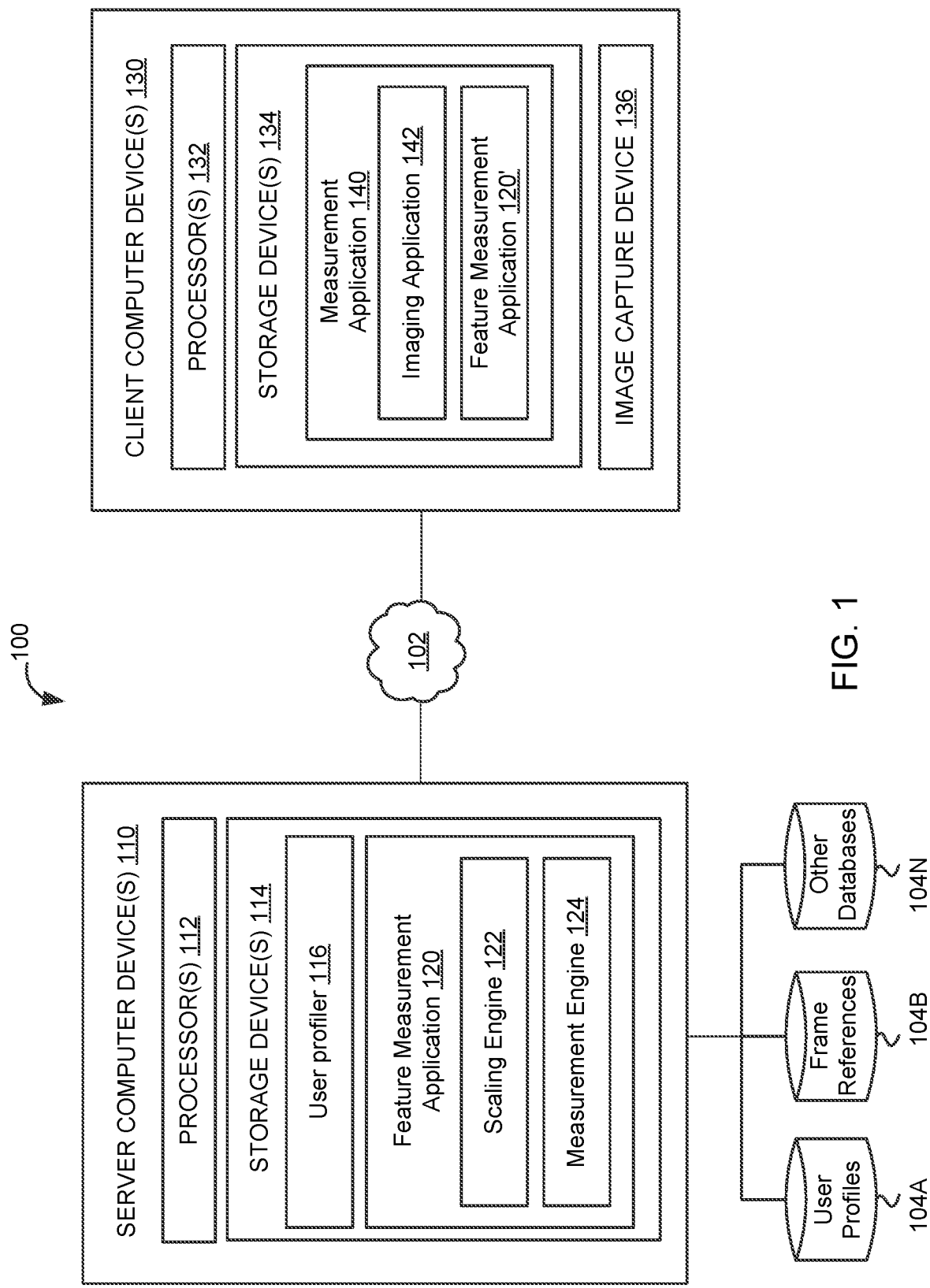
FIG. 1 illustrates a system of providing custom-fitted and styled eyewear based on user-provided images and preferences, according to an implementation of the invention.

FIG. 1 illustrates a system 100 of providing custom-fitted and styled eyewear based on user-provided images and preferences, according to an implementation of the invention. System 100 may be used to provide a custom-fitted and styled wearable item such as eyewear based on measurements made from a user-provided image of the user wearing the wearable item that is overlaid onto and resized based on a predefined reference image that includes a wearable item representation. The wearable item representation may include a graphical representation (e.g., a wireframe, a Computer Aided Design, a sketch, etc.), an actual image (e.g., a photograph), and/or other representation of the wearable item by itself (e.g., not worn). The predefined reference image may be full-scale such that measurements that are made using the image of the predefined reference are 1:1 with the actual wearable item.

System 100 may cause an actual wearable item to be provided (e.g., shipped) to a user, who wears the actual wearable item, obtains one or more images of the user wearing the actual wearable item, and provides the one or more images for processing. The system may compare a user-provided image to a predefined reference image that corresponds to the wearable item being worn by the user. For example, the system may overlay and resize a user-provided image with the predefined reference image so that the actual wearable item worn by the user in the user-provided image matches (the size of) the wearable item representation in the predefined reference image. Because the scale and/or dimensions of the predefined reference image are known, one or more measurements associated with the user may be made when the user-provided image is matched with the predefined reference image as if the measurements were made directly on the user wearing the wearable item. The one or more measurements may be made based on an anatomical feature (e.g., a pupil) of the user in relation to the wearable item.

Having provided a high level overview of examples of uses and implementations of system 100, attention will now be turned to various system components that facilitate these and other implementations of the invention.

System Components

System 100 may include one or more databases 104, one or more server computer devices 110, one or more client computer devices 130, and/or other components. The one or more databases may include a user profile database 104A, a frame reference database 104B, and/or other databases 104N.

User profile database 104A may store the previously described user profile information. Frame reference database 104B may store predefined reference images that each include a representation of a wearable item such as an eyeglass frame (which may include actual eyeglass frames—e.g., a photograph of the eyeglass frame—a representation of the eyeglass frame—e.g., a wireframe, CAD, or other representation). The eyewear retailer may obtain store a corresponding predefined reference image for each eyeglass frame sold by the eyewear retailer. For example, the eyewear retailer may obtain a full-scale (1:1) image of an eyeglass frame. Alternatively or additionally, the eyewear retailer may measure various reference points (e.g., top of frame to bottom of frame) to obtain reference measurements. In this manner, the predefined reference may have a known scale and/or dimensions. An overlay of the predefined reference image and a user-provided image may be used to scale the user-provided image.

Server computing device 110 may be communicably coupled to client computing device 130 via a network 102. Server computing device 110 may generally be under the control of the eyewear retailer, while client computing device 130 may generally be under the control of a user (e.g., a customer of the eyewear retailer) seeking to obtain eyewear. Server computing device 110 and client computing device 130 may each be programmed by computer program instructions. As used herein, for convenience, the various instructions will be described as performing an operation, when, in fact, the various instructions program server computing device 110 and/or client computing device 130 to perform the operation.

Client Computing Device 130

Client computing device 130 may include one or more physical processors 132, one or more storage devices 134, one or more image capture devices 136, and/or other components. Processor(s) 132 may be programmed by one or more computer program instructions, which may be stored in storage device(s) 134. For example, processor(s) 132 may be programmed by a measurement application 140. In a particular example, measurement application 140 may be a mobile application made available or provided by the eyewear retailer for execution on a user's mobile device. Other types of applications executed on other types of devices may be used as well.

Measurement application 140 may include an imaging application 142, a feature measurement application 120' (which may be a client device version and include one or more of the functions of feature measurement application 120 executing on a server computing device 110), and/or other instructions. Measurement application 120' may include some or all of the functions of feature measurement application 120.

Figure 3:
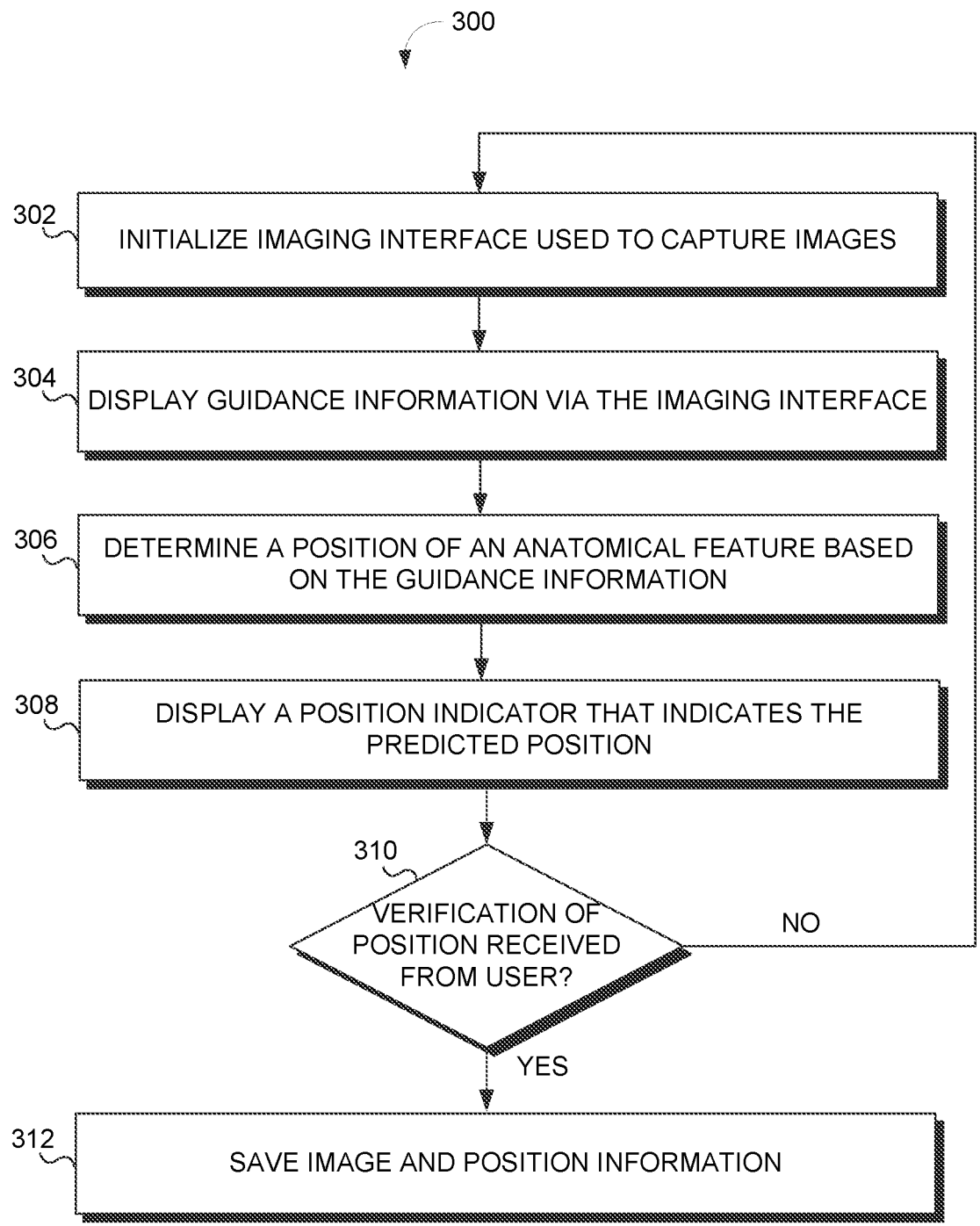
FIG. 3 depicts a process of generating an image of a user wearing a frame for determining custom measurements based on the image, according to an implementation of the invention.
Figure 4A:
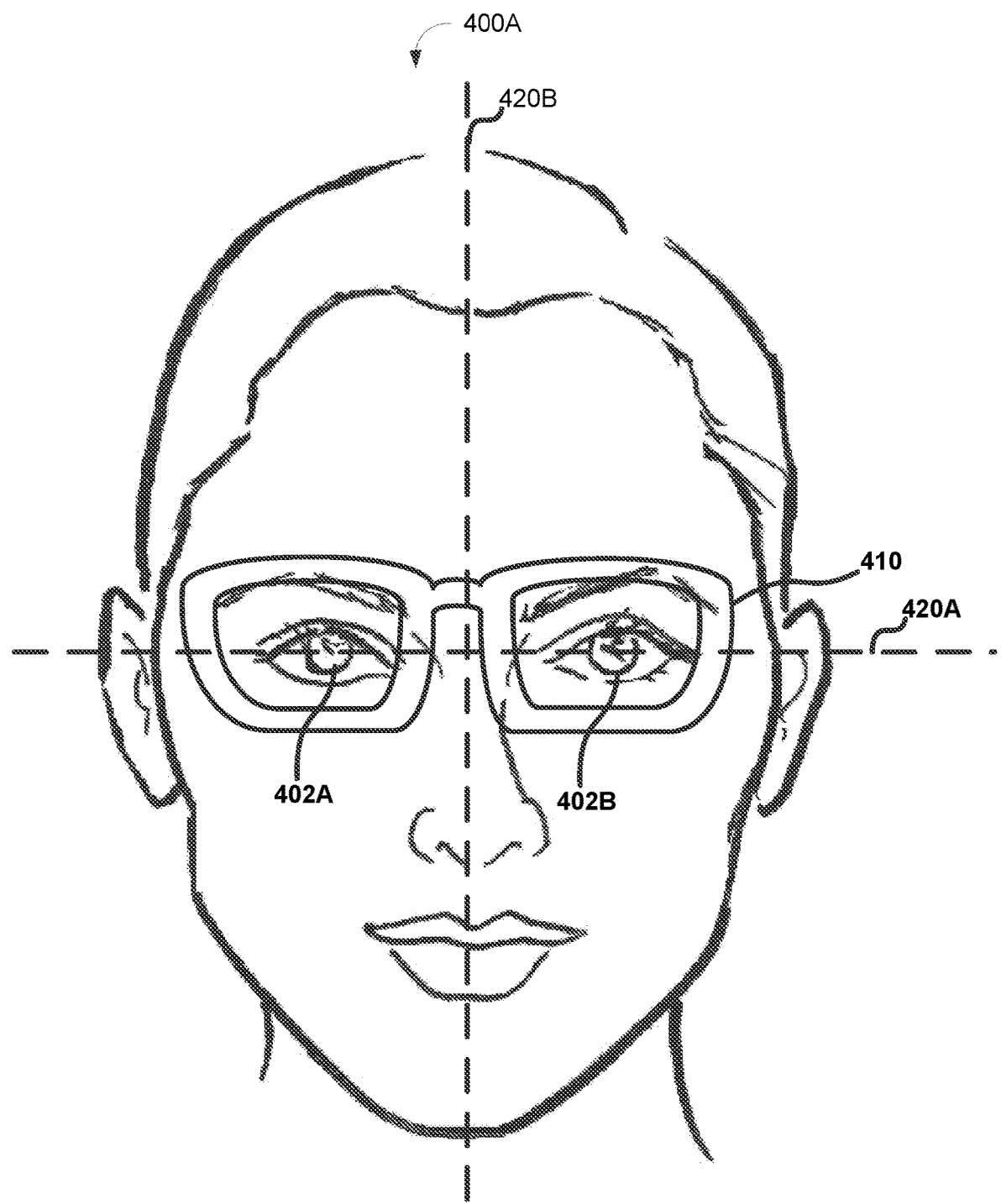
FIG. 4A depicts an imaging interface having guidance information to assist a user to take an image, according to an implementation of the invention.
Figure 4B:
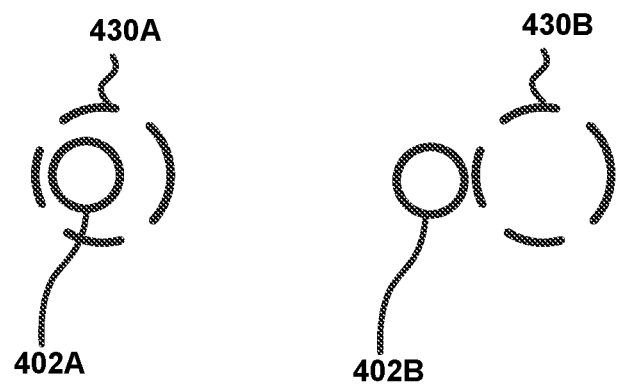
FIG. 4B depicts position indicators that indicate a predicted position of an anatomical feature displayed on the imaging interface that is incorrect and will not be verified by the user, according to an implementation of the invention.
Figure 4C:
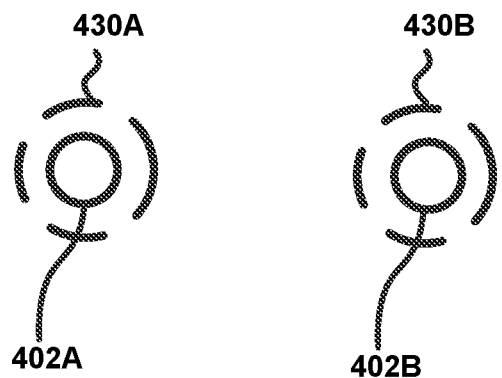
FIG. 4C depicts position indicators that indicate a predicted position of an anatomical feature displayed on the imaging interface that is correct and will be verified by the user, according to an implementation of the invention.

In an implementation, using image capture device 136, imaging application 142 may obtain an image of a user wearing an eyeglass frame. The image may be used by feature measurement application 120 (and/or 120') to obtain one or more measurements for generating custom-fitted lenses for the eyeglass frame. In an implementation, imaging application 142 may assist the user to take an appropriate image using one or more processes for generating the image. For example, FIG. 3 illustrates a process of generating such images and FIGS. 4A, 4B, and 4C illustrate user interfaces (or portions thereof) for generating such images.

Server Computing Device 110

In an implementation, server computing device 110 may receive a user-provided image of a user wearing an eyeglass frame, scale the user-provided image based on an overlay with a predefined reference image, and obtain one or measurements used to custom-fit lenses to the eyeglass frame. To accomplish these and other functions, server computing device 110 may include one or more physical processors 112, one or more storage devices 114, and/or other components. Processor(s) 112 may be programmed by one or more computer program instructions, which may be stored in storage device(s) 114. For example, processor(s) 112 may be programmed by a feature management application 120.

As previously described, one or all of the operations of feature management application 120 may be executed at client computing device 130. As such, in some implementations, through its version of feature management application 120 (feature management application 120'), client computing device 130 may obtain the one or more measurements as well. In an implementation, feature management application 120 (and 120') may include a scaling engine 122, a measurement engine 124, and/or other instructions.

Figure 5:
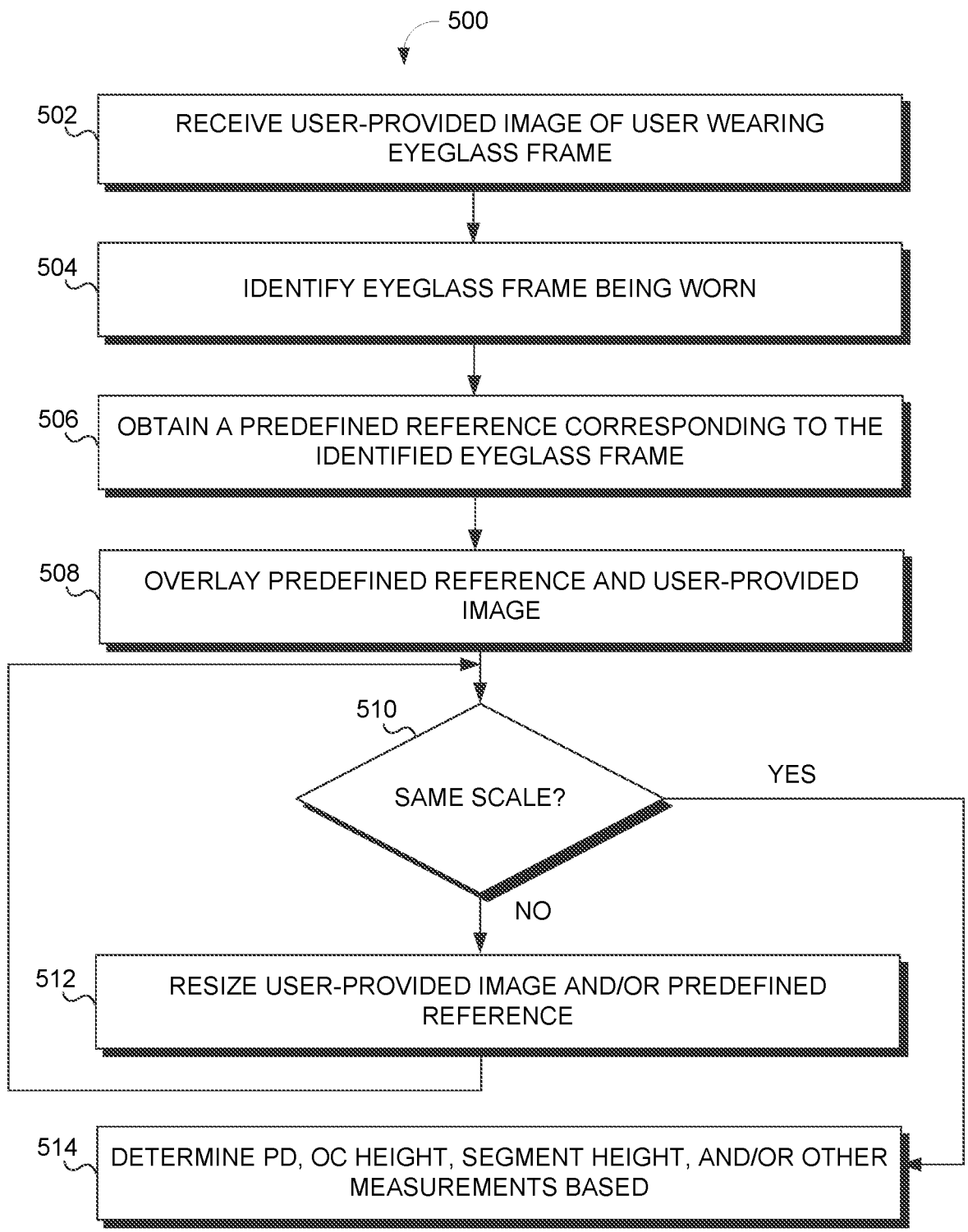
FIG. 5 depicts a process of determining custom measurements for eyewear based on an overlay of a reference image and a user-provided image, according to an implementation of the invention.

In an implementation, scaling engine 122 may scale (e.g., resize) a user-provided image in which a user is wearing an eyeglass frame with respect to a predefined reference, such as a previously taken image of the eyeglass frame, wherein the image is associated with a known scale or dimension. Because the predefined reference has a known scale or dimension, it may be used to scale the user-provided image and measure the PD, OC height, segment height, and/or other measurements related to the user-provided image. FIG. 5 illustrates a process of scaling a user-provided image based on a predefined reference image and FIGS. 6A, 6B, and 6C respectively illustrate examples of a user-provided image, a predefined reference image, and an overlay of the user-provided image and the predefined reference image.

Figure 7:
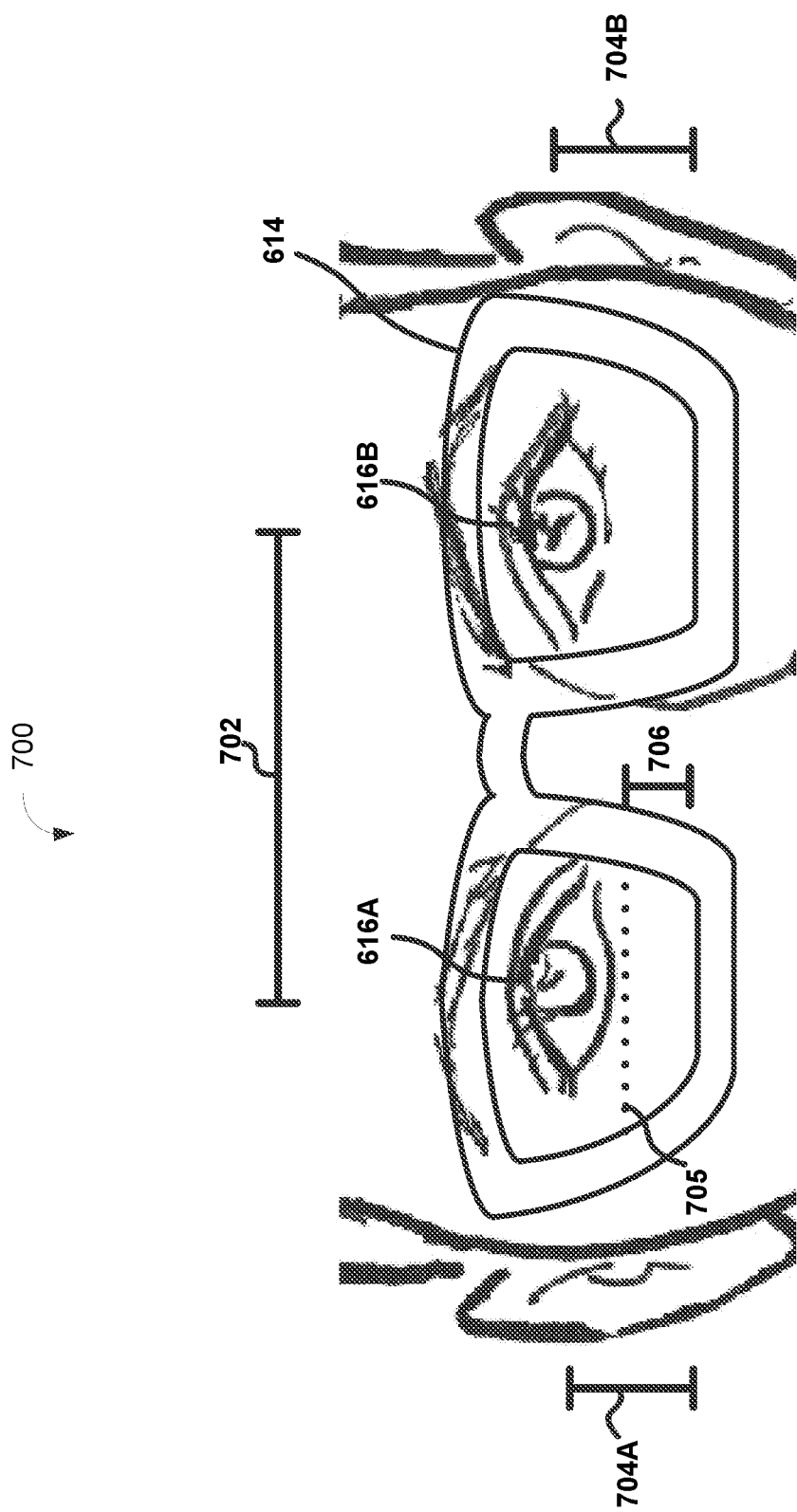
FIG. 7 depicts a two-dimensional view of a user-defined image that is scaled (e.g., resized) based on a predefined reference image to obtain one or more measurements, according to an implementation of the invention.

In an implementation, measurement engine 124 may determine PD, OC height, segment height, and/or other measurements based on a user-provided image that has been resized using a predefined reference image. For example, FIG. 7 depicts a two-dimensional view 700 of a user-provided image that is scaled (e.g., resized) based on a predefined reference image to obtain one or more measurements, according to an implementation of the invention. As illustrated, two-dimensional view 700 is cropped to illustrate one or more measurements that are taken based on a user-provided image that is scaled.

Measurement engine 124 may determine the one or more measurements using image processing techniques, such as analyzing pixel colors and/or textures to determine a location of various points in an image from which measurements are made. In an implementation, measurement engine 124 may be aided by a human operator to determine the measurements and/or the various points. For example, measurement engine 124 may receive indications from the user that mark measurement positions such as a center of a pupil, a bottom portion of frame 614, and/or other positions.

In an implementation, measurement engine 124 may determine a position of an anatomical feature 616, such as a pupil. In an implementation, in addition to or instead of image processing techniques, measurement engine 124 may determine a position of a pupil and its center point based on the predicted position of a pupil. For example, the center of the predicted position may be determined to be the center of the pupil 616. Measurement engine 124 may determine a PD 702 based on the center points of each of the pupils 616. Measurement engine 124 may determine an OC height 704A and 704B based on respective center points of the pupils and a bottom of frame 614. In implementations in which progressive lenses, bifocal, trifocal, and the like, measurement engine 124 may determine a Segment Height 706 based on a bottom portion of frame 614 and a segment 705 (e.g., for a bifocal lens, a trifocal lens, a progressive lens, etc.).

Examples of System Architectures and Configurations

Various system architectures may be used. For instance, a client computing device 130 may be programmed to guide users to take pictures of users wearing eyeglass frames. In some implementations, for example, an eyewear retailer may provide or make available an application (e.g., a mobile application) that is executed on a user's computing device (e.g., smartphone, tablet, laptop, etc.). Server computing device 110 may receive the user-provided image from the client computing device 130, resize/scale the user-provided image based on a predefined reference, and obtain PD, OC height, segment height, and/or other measurements based on the resized image.

It is noted, however, that the foregoing is described by way of illustration and not limitation. Client computing device 130 may perform one or more of the functions of server computing device 110 and vice versa. In a particular example, client computing device 130 may be programmed to obtain the one or more measurements as well. Additionally, the term "server" and "client" should not be viewed as limiting, as traditional "server-client" architecture need not be used. For example, a peer-to-peer or other computer communication technique may be used between the server computing device 130 and server computing device 110.

The one or more processors 112, 132 may each include one or more physical processors that are programmed by computer program instructions. The various instructions described herein are exemplary only. Other configurations and numbers of instructions may be used, so long as the processor(s) 112, 132 are programmed to perform the functions described herein.

Furthermore, it should be appreciated that although the various instructions are illustrated in FIG. 1 as being co-located within a single processing unit, in implementations in which processor(s) 112, 132 includes multiple processing units, one or more instructions may be executed remotely from the other instructions.

The description of the functionality provided by the different instructions described herein is for illustrative purposes, and is not intended to be limiting, as any of instructions may provide more or less functionality than is described. For example, one or more of the instructions may be eliminated, and some or all of its functionality may be provided by other ones of the instructions. As another example, processor(s) 112, 132 may be programmed by one or more additional instructions that may perform some or all of the functionality attributed herein to one of the instructions.

The various instructions described herein may be stored in a storage device 114, 134, which may comprise random access memory (RAM), read only memory (ROM), and/or other memory. The storage device may store the computer program instructions (e.g., the aforementioned instructions) to be executed by processor 112, 132 as well as data that may be manipulated by processor 112, 132. The storage device may comprise floppy disks, hard disks, optical disks, tapes, or other storage media for storing computer-executable instructions and/or data.

The various components illustrated in FIG. 1 may be coupled to at least one other component via a network, which may include any one or more of, for instance, the Internet, an intranet, a PAN (Personal Area Network), a LAN (Local Area Network), a WAN (Wide Area Network), a SAN (Storage Area Network), a MAN (Metropolitan Area Network), a wireless network, a cellular communications network, a Public Switched Telephone Network, and/or other network. In FIG. 1 and other drawing Figures, different numbers of entities than depicted may be used. Furthermore, according to various implementations, the components described herein may be implemented in hardware and/or software that configure hardware.

The various databases 104 described herein may be, include, or interface to, for example, an Oracle™ relational database sold commercially by Oracle Corporation. Other databases, such as Informix™, DB2 (Database 2) or other data storage, including file-based, or query formats, platforms, or resources such as OLAP (On Line Analytical Processing), SQL (Structured Query Language), a SAN (storage area network), Microsoft Access™ or others may also be used, incorporated, or accessed. The database may comprise one or more such databases that reside in one or more physical devices and in one or more physical locations. The database may store a plurality of types of data and/or files and associated data or file descriptions, administrative information, or any other data.

Providing Custom-Fitted and Styled Eyewear to Users

Figure 2:
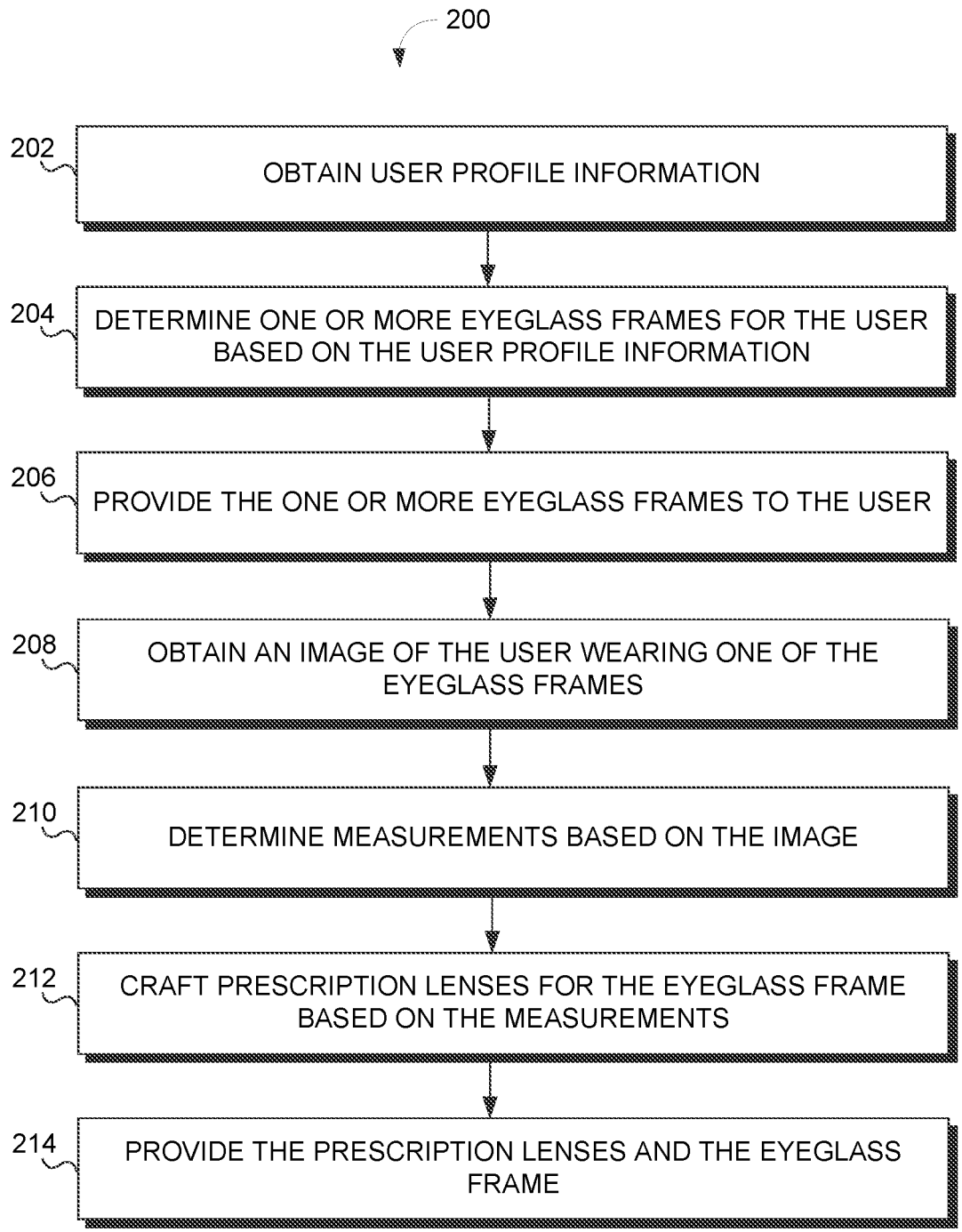
FIG. 2 depicts a process of providing custom-fitted and styled eyewear based on user-provided images and preferences, according to an implementation of the invention.

FIG. 2 depicts a process 200 of providing custom-fitted and styled eyewear based on user-provided images and preferences, according to an implementation of the invention. In an operation 202, user profile information may be obtained. The user profile information may include information that describes a user and may be used to select custom-styled eyeglass frames. For example, the user profile information may include, without limitation, identifying information (e.g., a name), demographic information (e.g., a gender, an ethnicity, an age, residence address, etc.), preference information that indicates user preferences (e.g., preferred colors, styles, etc.), an initial set of one or more images of a user used for style selection (not to be confused with user-provided images used for measurements, described below), and/or other information that describes the user. Once received, the user profile information may be stored and updated as necessary in a database such as in user profiles 104.

In an operation 204, the eyewear retailer (e.g., a stylist working for the eyewear retailer) may determine one or more frame styles and/or colors that, in the stylists' view, would be suitable for the user based on the user preference information. Alternatively or additionally, the user preference information may expressly indicate a preferred frame style (e.g., after perusing an online catalog of frame styles offered by the eyewear retailer). In any event, a set of one or more eyeglass frames may be selected for the user. An identification of each of the selected eyeglass frames may be stored in association with user identifying information so that the system may later retrieve this information.

In an operation 206, the eyewear retailer may provide the set of eyeglass frames to the user. For example, the eyewear retailer may ship the set of eyeglass frames to the user's home or other address (in brick-and-mortar implementations, the set of eyeglass frames may simply be worn by the user in-store). After having tried on each of the set of eyeglass frames, the user may select a favorite one (or more) to purchase. In an implementation, the eyeglass frames may be sample frames that, upon selection of a preferred frame by the user, are returned to the eyewear retailer.

In an operation 208, the eyewear retailer may obtain an image of the user wearing a favorite eyeglass frame. An image may be associated with user identifying information and frame identification information. In this manner, the eyewear retailer may obtain an identity of both the user and the frame being imaged. The image may be used by the system for measurement processing and should not be confused with images used for styling purposes. An example of providing an interface for the user to take the image (e.g., via a camera-equipped device) is illustrated in FIG. 3, although other users may take these images as well.

In an operation 210, the eyewear retailer may process the images to determine one or more measurements used to construct lenses (e.g., prescription lenses) to be custom-fitted for the eyeglass frame.

In an operation 212, the eyewear retailer may craft (or have crafted) prescription lenses based on the measurements.

In an operation 214, the eyewear retailer may provide the prescription lenses and the eyeglass frame to the user. For instance, the eyewear retailer may assemble the prescription lenses and the eyeglass frame and provide the assembled combination to the user. Such provisioning, in some implementations, may be contingent upon return of the eyeglass frames that were provided by the eyeglass retailer in operation 206. It should be noted that one or more of the foregoing operations may be automated or at least semi-automated using one or more of the components of system 100.

Capturing an Image of a User to Obtain Measurements

FIG. 3 depicts a process 300 of generating an image of a user wearing a frame for determining custom measurements based on the image, according to an implementation of the invention. The various processing operations and/or data flows depicted in FIG. 3 (and in the other drawing figures) are described in greater detail herein. The described operations may be accomplished using some or all of the system components described herein and, in some implementations, various operations may be performed in different sequences and various operations may be omitted. Additional operations may be performed along with some or all of the operations shown in the depicted flow diagrams. One or more operations may be performed simultaneously. Accordingly, the operations as illustrated (and described in greater detail below) are exemplary by nature and, as such, should not be viewed as limiting.

In an operation 302, an imaging interface may be initialized. The imaging interface may allow a user to capture an image through an image capture device. In an implementation, a predefined calibration image (which should not be confused with the predefined reference image) may be imaged to obtain distance/scale calibration information. The predefined calibration image may include, for example, a pre-printed image that is mailed to the user, an electronic image that is communicated and then printed or displayed by the user and then imaged by the user for calibration.

In an operation 304, guidance information may be generated and displayed via the imaging interface. The guidance information may be used by the user to visualize where to line up an anatomical feature such as a pair of pupils when taking an image. FIG. 4A depicts an imaging interface 400A having guidance information (420A, 420B) that helps a user take an appropriate image that can be used to obtain measurements from the image. Imaging interface 400A may be used to align anatomical features (402A, 402B) (e.g., pupils) along guidance information 420A and center the anatomical features 402 about guidance information 420B.

Returning to FIG. 3, in an operation 306, a position of an anatomical feature based on the image and the guidance information may be determined. For example, a position of a pupil may be determined based on an intersection of the guidance information and a discrete set of pixels having a shape, size, color, and/or other configuration in an image that corresponds to a pupil (or other anatomical feature).

In an operation 308, a position indicator that indicates the predicted position may be displayed to the user for verification. A user may visually inspect the position indicator and verify whether or not the position indicator actually corresponds to the position of the anatomical feature. The position indicator may be displayed as a closed geometric shape or other image object to indicate a predicted position of a pupil. For example, a circle may be displayed for each predicted pupil position in the image. The user may then verify whether the predicted pupil positions are accurate. In an implementation, the system may determine a center of the pupil based on a center of the position indicator (e.g., center of the circles corresponding to the predicted positions of the pupils).

FIG. 4B depicts position indicators (430A, 430B) that indicate a predicted position of an anatomical feature (402A, 402B) displayed on imaging interface 400A that is incorrect and will not be verified by the user, according to an implementation of the invention. FIG. 4C depicts position indicators (430A, 430B) that indicate a predicted position of an anatomical feature (402A, 402B) displayed on imaging interface 400A that is correct and will be verified by the user, according to an implementation of the invention.

Returning to FIG. 3, in an operation 310, a determination of whether the user verified the predicted position may be made. For instance, responsive to a determination that the user did not verify the predicted position, processing may return to operation 302, in which an imaging interface may be initialized to attempt a new image capture. On the other hand, responsive to a determination that the user has verified the predicted position, processing may proceed to an operation 312, in which the image is saved so that measurements may be obtained based on the image. In an implementation, process 300 may communicate the image to server computing device 110, where the measurements are obtained. For example, process 300 may allow the user to send the image directly from a mobile application or the user may send the image to the server computing device via electronic mail and/or other communication channel.

Resizing User-Provided Images Based on a Predefined Reference Image

FIG. 5 depicts a process 500 of determining custom measurements for eyewear based on an overlay of a predefined reference and a user-provided image, according to an implementation of the invention. The various processing operations and/or data flows depicted in FIG. 5 (and in the other drawing figures) are described in greater detail herein. The described operations may be accomplished using some or all of the system components described herein and, in some implementations, various operations may be performed in different sequences and various operations may be omitted. Additional operations may be performed along with some or all of the operations shown in the depicted flow diagrams. One or more operations may be performed simultaneously. Accordingly, the operations as illustrated (and described in greater detail below) are exemplary by nature and, as such, should not be viewed as limiting.

In an operation 502, a user-provided image of a user wearing an eyeglass frame and frame identifying information may be received. The frame identifying information may be used to identify the eyeglass frame being worn. In an implementation, at least a portion of the user-provided image may be manually or automatically cropped so that only relevant portions of the image are processed.

Figure 6A:
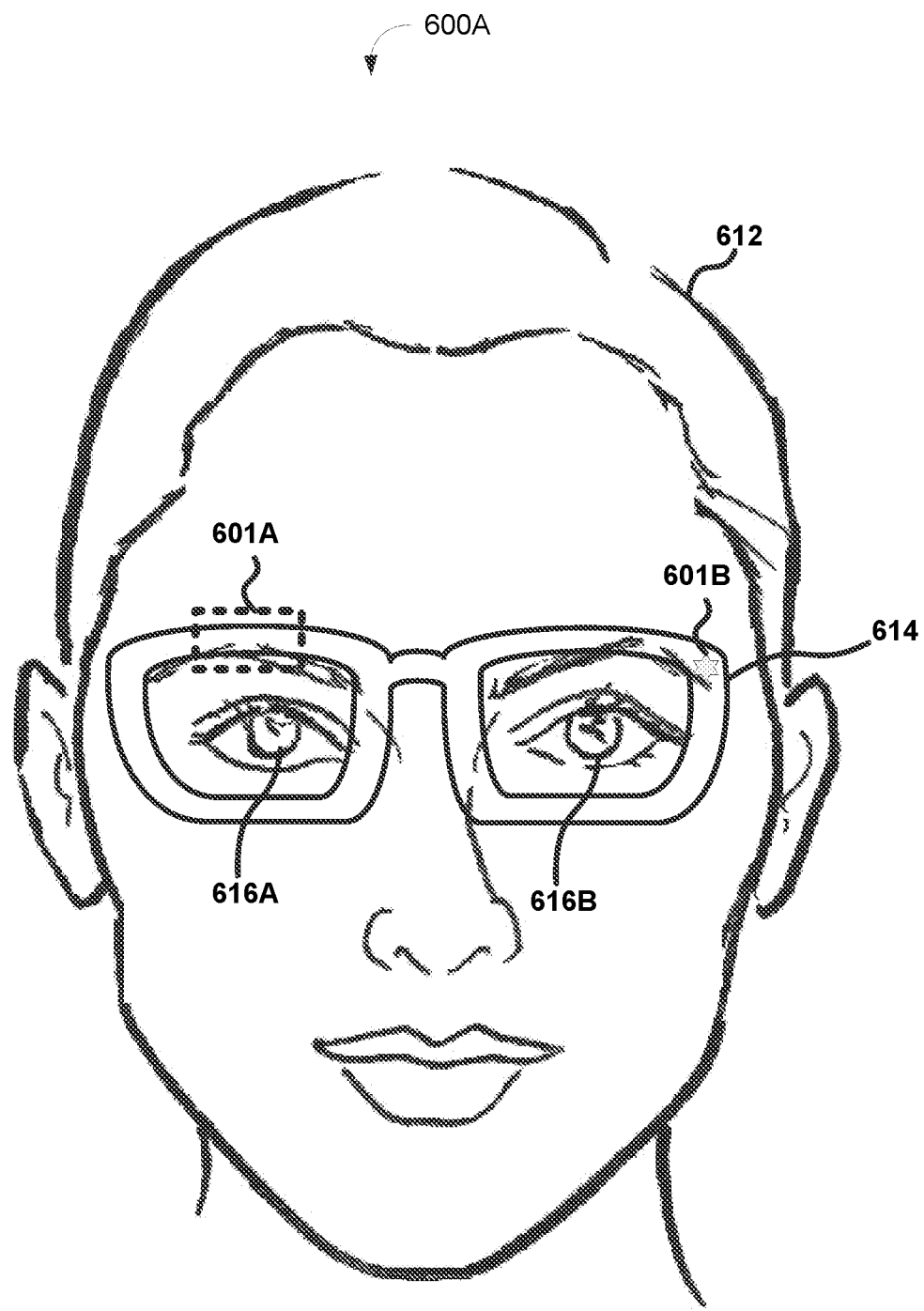
FIG. 6A depicts a user-provided image to be scaled and used to obtain measurements based on an overlaid predefined reference, according to an implementation of the invention.

FIG. 6A depicts a user-provided image 600A to be scaled and used to obtain measurements based on an overlaid predefined reference, according to an implementation of the invention. The user-provided image 600A may include an image of a user 612 wearing an eyeglass frame 614. In an implementation, eyeglass frame 614 may include one or more predefined reference points, such as a portion of an eyeglass frame 601A, a unique design element 601B, and/or other reference points. One eyeglass frame may include a set of predefined reference points that are different than those for another predefined reference. The user-provided image may include one or more anatomical features (616A, 616B) such as pupils. Although not illustrated in FIG. 6, user-provided image 600A may include one or more imaging interface features used to take the user-provided image. For example, user-provided image 600A may include (referring to FIGS. 4A and 4C) guidance information (420A, 420B), predicted position indicators (430A, 430B), and/or other information.

Returning to FIG. 5, in an operation 504, an identity of the eyeglass frame being worn by the user may be obtained based on the frame identifying information. For example, the frame identifying information may include a model name, a product identifier (e.g., a Stock Keeping Unit), and/or other information used to identify the eyeglass frame being worn. Alternatively or additionally, the frame identifying information may include the image itself, in which a human operator and/or computer image recognition techniques may be used to identify the eyeglass frame.

Figure 6B:
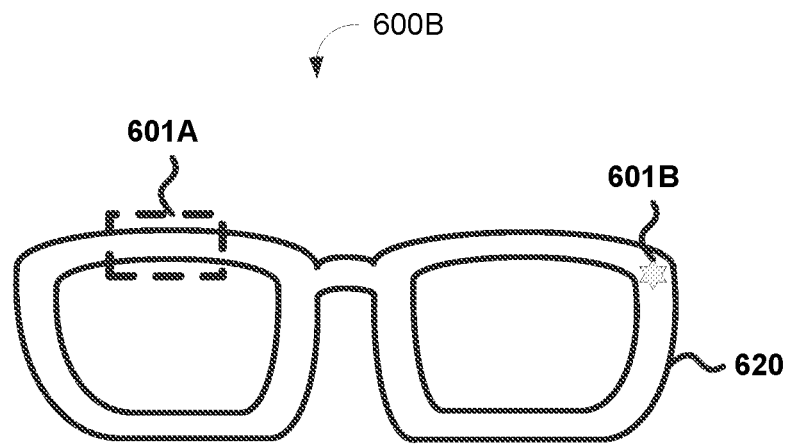
FIG. 6B depicts a predefined reference used to scale and obtain measurements related to a user-provided image, according to an implementation of the invention.

In an operation 506, a predefined reference image may be obtained based on the identity of the eyeglass frame being worn by the user in the user-provided image. The predefined reference image may be obtained from frame reference database 104B based on the identity of the eyeglass frame being worn by the user. FIG. 6B depicts a predefined reference image 600B that includes a wearable item representation 620 used to scale and obtain measurements related to a user-provided image, according to an implementation of the invention. As with its actual counterpart, wearable item representation 620 may include a portion 601A, a unique design feature 601B, and/or other features.

Wearable item representation 620 may be compared to user-provided image 600A in which user 612 is wearing eyeglass frame 614. Wearable item representation 620 and eyeglass frame 614 may have the same actual dimensions. However, the user may have taken user-provided image 600A at a zoom level such that the scale is different. Because wearable item representation 620 has a known scale and/or dimensions, it may be used to resize eyeglass frame 614 in order to measure positions of anatomical features 616 (e.g., pupils) with respect to eyeglass frame 614. For example, the PD, OC height, segment height, and/or other measurements may be made when the wearable item representation 620 is scaled with the user-provided image 600A.

Figure 6C:
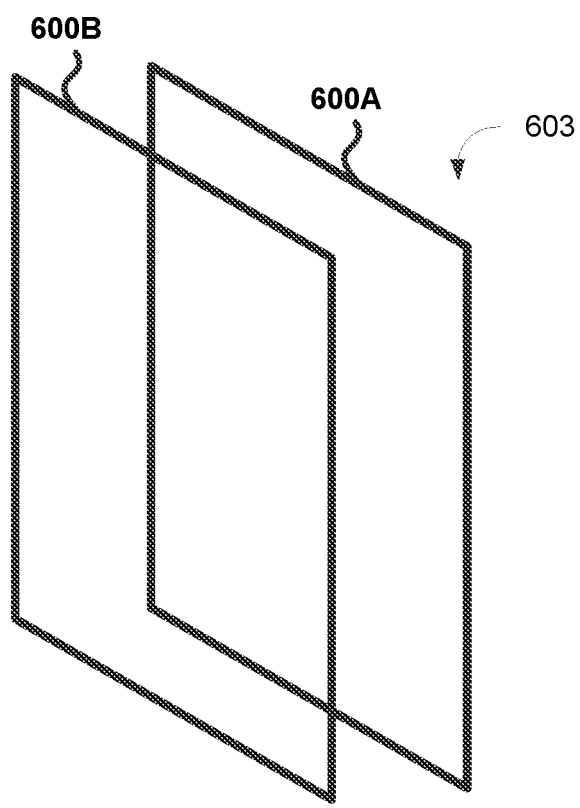
FIG. 6C depicts a perspective view of a predefined reference image overlaid with a user-provided image to scale and obtain measurements from the user-provided image, according to an implementation of the invention.

Returning to FIG. 5, in an operation 508, wearable item representation 620 may be overlaid with (e.g., on top or bottom of) user-provided image 600A, as schematically illustrated in FIG. 6C. FIG. 6C depicts a perspective view 603 of a predefined reference image 600B overlaid with a user-provided image 600A to scale and obtain measurements from the user-provided image.

Returning back to FIG. 5, in an operation 510, a determination of whether the wearable item representation 620 is scaled (and lined up) with eyeglass frame 614 may be made. Wearable item representation 620 is scaled (and lined up) with eyeglass frame 614 from user-provided image 600A if one or more of the reference points 602 in both the wearable item representation and user-provided image 600A line up or otherwise substantially match. "Substantially match" may include a match within a certain tolerance (e.g., +/− 10 percent of a dimension of a given reference point 602). Other tolerances may be used as well and the foregoing example is not intended to be limiting. Typically, though not necessarily, more than one reference point 602 (or the entire eyeglass frame 614) may be used to match wearable item representation 620 and eyeglass frame 614.

In an implementation, the scaling may be performed by comparing pixels of the predefined reference image 600B and user-provided image 600A. For instance, the scaling may include predicting the position of eyeglass frame 614 in user-provided image 600A based on image recognition techniques, tracking pixel positions in which eyeglass frame 614 is separate from the rest of user-provided image 600A (for instance, the pixels of the frame may be a different color or texture from the remaining portions of user-provided image 600A), and/or other image processing techniques.

In some implementations, a human operator may line up or assist lining up of wearable item representation 620 and eyeglass frame 614. For example, an application may be provided that guides a user to scale wearable item representation 620 and eyeglass frame 614 by displaying the overlay to the user and having the user scale up or down the user-provided image 600A. In these implementation, process 500 may receive input from a user to scale up or down user-provided image 600A.

Returning to operation 510, responsive to a determination that wearable item representation 620 is not scaled with eyeglass frame 614, a size of user-provided image 600A and/or predefined reference image 600B may be adjusted by a scaling factor in an operation 512. The scaling factor may include a percentage (e.g., increase or decrease size by 5%, or 1.05x), and/or other scaling factor. The scaling factor may be variable. For instance, the scaling factor may be iteratively reduced as the user-provided image 600A and predefined reference image 600B (e.g., their respective images) get closer and closer to the same scale. In this manner, size adjustment may be fine-tuned. Alternatively, the scaling factor may be increased if the user-defined image 600A and predefined reference image 600B are not sufficiently close together in scale after (n) number of attempts. In this manner, the size adjustment may be coarse-tuned to reduce processing cycles.

Typically, though not necessarily, the size of user-provided image 600A may be adjusted up or down to match predefined reference image 600B. In this manner, eyeglass frame 614 in user-provided image 600A may be adjusted to match the same scale and dimensions of wearable item representation 620 in predefined reference image 600B, allowing measurement of the PD, the OC height, the segment height, and/or other measurement. After size adjustment, processing may return to operation 510, where a determination of whether wearable item representation 620 is scaled with respect to eyeglass frame 614 may be made.

Responsive to a determination that wearable item representation 620 is scaled with respect to eyeglass frame 614, the PD, OC height, segment height, and/or other measurements may be determined in an operation 514.

Adjusting Determined Measurements Based on Camera Distance

In an implementation, one or more of the determined measurements may be adjusted based on distance information that indicates a distance between a user's face and an imaging device used to generate the image. For example, a PD measurement determined from a user-provided image may be adjusted based on the distance between a user's face and the camera that took the user-provided image (hereinafter, "camera distance" for convenience). This is because depending on a distance from an object on which a user focuses, the pupils may rotate inward or outward, affecting a length between the pupils.

The system may account for such rotation by adding a PD adjustment value, which may be variable depending on the camera distance. For example, for camera distances equal to or greater than twenty feet, the PD adjustment value may be zero. This is because distances of twenty feet or more may typically (e.g., for most users) result in little or no pupil rotation (i.e., both pupils are facing substantially straight-ahead). For a camera distance of five feet, the PD adjustment value may be 1.5 millimeters (mm). For a camera distance that is reading length, or approximately one to two feet, the PD adjustment value may be 3.0 mm. As would be appreciated, other PD adjustment values (including ranges of camera distances and ranges of PD adjustment values) may be used for these and other camera distances as well. Furthermore, the PD adjustment values may be predefined for all users or a particular user. In an implementation, the PD adjustment value may be based on a function that correlates the PD adjustment value and camera distance. Such a function may be linear, curvilinear, and/or otherwise be suited to obtain a particular PD adjustment value for a particular camera distance. At any rate, measurement engine 124 may adjust the measured PD with using a PD adjustment value that is based on a camera distance.

The system may obtain the camera distance in various ways. For example, measurement engine 124 may obtain the camera distance from a user. In this example, the user may provide the camera distance along with the user-provided image. If so equipped, a user device may provide a camera distance determined from a range finder or other automatic distance device.

In an implementation, measurement engine 124 may obtain the camera distance from imaging application 142. For example, imaging application 142 may provide an imaging interface that includes guidance information such as circles (or other graphical indicia) used by the user to line up the pupils. The circles may be space apart such that (for most users), if the pupils line up with the circles, then a particular camera distance (e.g., five feet) is assumed. If the user takes an image (upon verifying that the user's pupils falls within the circles), then imaging application 142 may provide the particular camera distance to measurement engine 124 (and/or measurement engine 124 may simply assume the particular camera distance because imaging application 142 is programmed to take images from the particular camera distance).

Applying a Scaled User-Provide Image to Different Eyeglass Frames

In an implementation, a user-provided image (in which a user is wearing an eyeglass frame) that was previously scaled using a predefined reference image as disclosed herein may be used to determine measurements for another eyeglass frame not worn by the user. For example, the user may decide to purchase a second eyeglass frame after having worn the first eyeglass frame, which was used to obtain one or more measurements. Scaling engine 122 may scale a second predefined reference image corresponding to the second eyeglass frame using the user-provided image that was scaled for the first eyeglass frame. For example, a portion of the first eyeglass frame (e.g., a nose bridge portion) in the scaled user-provided image may be aligned (zoomed/panned/etc.) with a corresponding portion (e.g., a nose bridge portion) of the second eyeglass frame of the second predefined reference image. Such scaling may be performed by scaling engine 122 as described herein. Because various dimensions and measurements are known from the scaled user-provided image, such dimensions and measurements may be used to determine dimensions and measurements of the second eyeglass frame. In this manner, the user may flexibly select different frames or other wearable items that have not yet been worn by the user so long as the system has already measured the user using at least one eyeglass frame worn by the user that was scaled according to its corresponding predefined reference image.

Using Known Dimensions to Determine Measurements

In an implementation, the system may determine the one or more measurements based on a known dimension associated with an eyeglass frame (or other wearable item) being worn by the user. For instance, a distance between lenses ("DBL") value may be imprinted on a given eyeglass frame. If the user provides (and the system receives) the DBL value, feature measurement application 120 may use this value as a reference to scale other dimensions in a user-provided image of the user wearing the eyeglass frame and obtain the one or more measurements based on the scaling. Other known dimensions may be used as well, including user-provided dimensions (e.g., dimensions that the user measures and provides).

In some implementations, feature measurement application 120 may use the DBL (or other known dimension) alone when a corresponding eyeglass frame is unknown to the system (e.g., does not have a corresponding reference image). When the eyeglass frame is known to the system, the DBL may be used in combination with other scaling techniques described herein. For example, feature measurement application 120 may use the DBL (if available from the user, frame references database, and/or other source) as an additional data point when scaling a user-provided image with a predefined reference image. Alternatively or additionally, feature measurement application 120 may use the DBL as a validation check to validate scaling performed on a user-provided image.

Other implementations, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A system for obtaining images of a user wearing an eyeglass frame, wherein the images are used to measure the user to customize vision-corrective lenses for the user, the system comprising:
    a computer system comprising one or more physical processors programmed with computer program instructions to:
        generate a user interface used to take one or more images of the user wearing a wearable item;
        display, via the user interface, guidance information that assists the user to align one or more anatomical features of the user, the guidance information comprising one or more visual cues that should intersect the one or more anatomical features; and
        receive an indication from the user that the guidance information and the one or more anatomical features of the user are aligned, wherein the computer system is further programmed to:
        determine a position of the one or more anatomical features based on the guidance information and the image;
        display a position indicator at the determined position in relation to the one or more anatomical features, wherein the position indicator indicates the determined position;
        provide a prompt that asks the user to verify whether the position indicator is correctly placed with respect to the one or more anatomical features; and
        save the image in association with the determined position responsive to a determination that the user has verified the position indicator is correctly placed.

2. The system of claim 1, wherein the one or more anatomical features comprises a pupil.

3. The system of claim 2, wherein the position indicator is displayed as a closed geometric shape around the pupil.

4. The system of claim 3, wherein a center of the pupil is determined based on a center of the closed geometric shape.

5. The system of claim 3, wherein the closed geometric shape comprises a circle.

6. The system of claim 1, wherein the computer system is further programmed to:

take an image of a predefined scaling image; and
determine a scale of the image of the user based on the predefined scaling image.

7. The system of claim 1, wherein the wearable item comprises an eyeglass frame, and wherein the computer system is further programmed to:
    determine an identification of the eyeglass frame being worn by the user, based on the image; and
    determine one or more measurements used to construct vision-corrective lenses for the eyeglass frame, based on a comparison of a size of the eyeglass frame from the image and a size of the eyeglass frame from a predefined reference image.

8. The system of claim 7, wherein the one or more measurements comprise a pupillary distance ("PD"), an ocular center ("OC") height, and/or a segment height.

9. The system of claim 7, wherein the predefined reference image comprises an image of a representation of at least a portion of the eyeglass frame or an actual image of at least a portion of the eyeglass frame.

10. The system of claim 1, wherein the computer system is further programmed to:
    provide the image of the user to a server computing device that makes one or more measurements based on the image of the user to construct vision-corrective lenses.

11. A method to obtain images of a user wearing an eyeglass frame, wherein the images are used to measure the user to customize vision-corrective lenses for the user, the method comprising:
    generating a user interface used to take one or more images of the user wearing a wearable item;
    displaying, via the user interface, guidance information that assists the user to align one or more anatomical features of the user, the guidance information comprising one or more visual cues that should intersect the one or more anatomical features; and
    receiving an indication from the user that the guidance information and the one or more anatomical features of the user are aligned, wherein receiving the indication comprises:
        determining a position of the one or more anatomical features based on the guidance information and the image;
        displaying a position indicator at the determined position in relation to the one or more anatomical features, wherein the position indicator indicates the determined position;
        providing a prompt that asks the user to verify whether the position indicator is correctly placed with respect to the one or more anatomical features;
        saving the image in association with the determined position responsive to a determination that the user has verified the position indicator is correctly placed.

12. The method of claim 11, wherein the one or more anatomical features comprises a pupil.

13. The method of claim 12, wherein the displaying a position indicator comprises displaying the position indicator as a closed geometric shape around the pupil.

14. The method of claim 13, wherein a center of the pupil is determined based on a center of the closed geometric shape.

15. A method to obtain one or more measurements used to construct vision-corrective lenses for an eyeglass frame, the method comprising:
    obtaining, with a computer system, a user-provided image comprising an image of a user wearing the eyeglass frame;

determining, with the computer system, at least a first dimension of a first part of the eyeglass frame in the user-provided image;

determining, with the computer system, an identification of the eyeglass frame being worn by the user;

obtaining, with the computer system, a predefined reference based on the identification, wherein the predefined reference is based on a visual feature of the eyeglass frame and wherein the predefined reference further comprises at least a second dimension;

and determining, with the computer system, one or more measurements used to construct the vision-corrective lenses, by scaling of the first dimension based on the second dimension.

16. The method of claim 15, wherein the one or more measurements comprise a pupillary distance ("PD"), an ocular center ("OC") height, and/or a segment height.

17. The method of claim 15, further comprising:
obtaining a camera distance associated with the user-provided image;
determining one or more adjustment values based on the camera distance; and
adjusting at least one of the one or more measurements based on the one or more adjustment values.

18. The method of claim 15, wherein the scaling comprises:
iteratively reducing or enlarging the size of the user-provided image until the eyeglass frame in the user-provided image substantially matches the size of the eyeglass frame in the predefined reference.

19. The method of claim 15, wherein the one or more measurements comprise a pupillary distance ("PD"), an ocular center ("OC") height, and a segment height.

20. The method of claim 15, wherein the one or more measurements comprise a pupillary distance ("PD") and an ocular center ("OC") height.

\* \* \* \* \*